(12) United States Patent
Schneider et al.

(10) Patent No.: US 6,704,470 B1
(45) Date of Patent: Mar. 9, 2004

(54) OPTOELECTRONIC GAS SENSOR BASED ON OPTODES

(75) Inventors: Joachim Schneider, Unterhaching (DE); Anton Pfefferseder, Sauerlach-Arget (DE); Andreas Hensel, Vaihingen (DE); Ulrich Oppelt, Zorneding (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/529,155

(22) PCT Filed: Jun. 29, 1999

(86) PCT No.: PCT/DE99/01884

§ 371 (c)(1),
(2), (4) Date: Jun. 22, 2000

(87) PCT Pub. No.: WO00/08447

PCT Pub. Date: Feb. 17, 2000

(30) Foreign Application Priority Data

Aug. 7, 1998 (DE) .......................................... 198 35 769

(51) Int. Cl.[7] .................................................. G02B 6/26
(52) U.S. Cl. ........................ 385/12; 250/227.14; 385/14
(58) Field of Search ...................... 385/12, 14, 129–132, 385/141–143; 250/227.14; 356/432–437

(56) References Cited

U.S. PATENT DOCUMENTS

| 4,755,667 A | 7/1988 | Marsoner et al. |
| 4,872,759 A | 10/1989 | Stich-Baumeister et al. |
| 5,177,352 A | 1/1993 | Carson et al. |
| 5,442,169 A | 8/1995 | Kunz |
| 5,737,457 A | 4/1998 | Saini et al. |
| 5,822,473 A | * 10/1998 | Magel et al. .................. 385/12 |
| 5,886,401 A | * 3/1999 | Liu ............................. 257/678 |

FOREIGN PATENT DOCUMENTS

EP  0 834 735  4/1998

OTHER PUBLICATIONS

Richard J. Polina et al., "A Field Hardened Optical Waveguide Hybrid Integrated–Circuit, Multi–Sensor Chemical Probe And Its Chemistry," 3105 SPIE 71–78.

* cited by examiner

Primary Examiner—John D. Lee
Assistant Examiner—Sarah U Song
(74) Attorney, Agent, or Firm—Kenyon & Kenyon

(57) ABSTRACT

An optoelectronic gas sensor based on optodes, where multiple separate photosensitive elements and an opto-transmitter located centrally between them are integrated into or onto a semiconductor substrate is characterized in that the photosensitive elements lie in one plane in the substrate, and together with a lateral emission area of the opto-transmitter emitting light laterally, they are covered by sections of the optode material whose thickness and refractive index are selected so that light emitted laterally from the emission area is guided to the photosensitive elements by total reflection in the optode material in each transmission branch. Such a chip-shaped gas sensor based on optodes can be implemented in a very small design, e.g., in an area of $2 \times 2$ mm$^2$ and a thickness of 250 $\mu$m.

20 Claims, 3 Drawing Sheets

OPTOELECTRONIC GAS SENSOR BASED ON OPTODES

FIELD OF THE INVENTION

The present invention relates to an optoelectronic gas sensor based on optodes as well as an electronic component for producing such an optoelectronic gas sensor.

BACKGROUND INFORMATION

An optoelectronic gas sensor is described in a technical article "A field hardened optical waveguide hybrid integrated-circuit, multi-sensor chemical probe and its chemistry" by Richard J. Polina et al. in SPIE, vol. 3105, pages 71–78. This known gas sensor based on optodes is diagramed schematically in FIG. 6, and its properties are described briefly below.

From an LED 33, a light bundle is divided vertically by two mirrors 35, 36 into two parts L1, L2 and reflected laterally, so it goes to a measuring segment 38 made of optode material and a reference segment 39. Light beam L2 passing through optode segment 38 is in turn reflected down vertically on a mirror surface 37, so it reaches the photosensitive surface of a first photodiode 32, while light beam L1 passing through reference segment 39 is reflected down vertically onto the photosensitive surface of another photodiode 31 at another mirror surface 34. Optode segment 38 and reference segment 39, mirror surfaces 34–37 and photodiodes 31 and 32 are arranged symmetrically about LED 33 which is arranged at the center. The optode material of measuring segment 38 is exposed opposite the gas to be measured (arrow), so this gas has access through an opening provided in the chip casing (not shown).

FIG. 7 shows schematically a gas measuring sensor 30 equipped with three successive sensor units 301, 302 and 303 according to FIG. 6.

Due to the method of coupling and reflection of light bundles L1 and L2 and mirror surfaces 34–37, first from the vertical into the lateral direction and then from the lateral back into the vertical direction, the known gas sensor chip shown in FIG. 6 and described in the technical article cited above is relatively long and broad (e.g., 3 cm long and 0.35 cm broad), so a gas measuring sensor 30 according to FIG. 7 constructed using multiple gas sensor chips 301–303 arranged in successive rows turns out to be rather long. In addition, such a known gas sensor chip and gas measuring sensor 30 implemented with it is relatively expensive. Furthermore, various aging phenomena on separate chips 301–303 can lead to unwanted measurement errors.

SUMMARY OF THE INVENTION

An object of the present invention is to make possible an improved optoelectronic gas sensor based on optodes, so that it will be less expensive and will have much smaller dimensions, and so that an electronic component according to the present invention can be made available for manufacturing an optoelectronic gas sensor without requiring additional optical components such as mirrors and prisms.

According to a first embodiment of the present invention, the object is achieved by providing an optoelectronic gas sensor based on optodes, where multiple separate photosensitive elements and an opto-transmitter located centrally between them are integrated into or onto a semiconductor substrate; this is characterized in that the photosensitive elements lie in one plane in the substrate, and together with a lateral emission area of the opto-transmitter emitting light laterally they are covered by sections of the optode material whose thickness and refractive index are selected so that light emitted laterally from the emission area is guided to the photosensitive elements by total reflection in the optode material in each transmission branch.

According to a second embodiment of the present invention, an optoelectronic gas sensor based on optodes achieving the above object is made available, where multiple separate photosensitive elements and an opto-transmitter located centrally between them are integrated into or onto a semiconductor substrate; this is characterized in that the photosensitive elements lie in one plane in the substrate and are each covered by a section of the optode material, the opto-transmitter is spaced a distance away from the sections of the optode material through an annular gap, and the thickness of the optode material is much smaller than the height of the opto-transmitter, so the light emitted by the opto-transmitter is emitted into air and then reaches the photosensitive elements through the optode material either directly or after being reflected on the inside walls of a casing surrounding the gas sensor chip.

One of the photosensitive elements and the layer covering it may form a reference segment. The optode material of the measuring segments is made of a gas-sensitive polymer carrier material to which is added at least one indicator substance from the group of compounds including, for example, azobenzenes, acetophenones, corrins, porphyrins, phthalocyanines, macrolides, porphyrinogens, nonactin, valinomycin and/or complexes thereof with transition metals of secondary groups I–II and V–VIII. However, the layer covering the reference segment may be made of a polymer carrier material without any added indicator substance.

In an embodiment of a layout according to the present invention, the photosensitive elements of the optoelectronic gas sensor with the sections of the optode material covering them or with the polymer carrier layer covering the reference segment may be arranged in sectors with central symmetry around the opto-transmitter. For example, in this way four symmetrical transmission branches may be formed, including three sensor segments and one reference segment.

The chip forming the optoelectronic gas sensor may be designed to be square, pentagonal, hexagonal, heptagonal or octagonal or even circular, for example. Of course, such an optoelectronic gas sensor may also include less than or more than four transmission branches.

With an optoelectronic gas sensor implemented according to the first embodiment, the individual transmission branches are separated by barriers, so that the individual transmission branches are not influenced optically by the stray light coming from the optode material. The height of these barriers may be selected to be approximately the same as the height of the central photosensor. In addition, all locations on the chip that are not photosensitive may be mirrorized if necessary, likewise the side walls of the barriers.

The substrate of the chip may be made of n-type silicon, and the photosensitive elements may be made of p-type regions of silicon integrated into the n-type silicon substrate. In this way, the photosensitive elements form photodiodes. The opto-transmitter is preferably an LED, but multiple LEDs may also be used to define the wavelength.

The thickness of the optode material over the photosensitive elements may be 200 $\mu$m to 300 $\mu$m and preferably in the range of 220 $\mu$m to 260 $\mu$m.

With an optoelectronic gas sensor constructed according to the second embodiment of the present invention, the thickness of the optode material is much less than the height of the LED and amounts to approx. 5 µm to 20 µm, preferably 5 µm to 10 µm, while the height of the opto-transmitter (LED) is much greater, and may amount to approx. 300 µm.

To produce an optoelectronic gas sensor, an electronic component provided for this purpose may be designed so that multiple separate photosensitive elements are integrated into or onto a semiconductor substrate in sectors with central symmetry while maintaining a certain mutual spacing; a thin dielectric insulation layer covers all the photosensitive semiconductor areas; contact openings are provided with contacts to the photosensitive semiconductor elements at defined peripheral locations on the photosensitive semiconductor elements; and metallized strips are provided in the spaces between the photosensitive elements leading to a central contact pad for connecting the LED functioning as the opto-transmitter.

In this way, four equally large photodiodes having a common cathode formed by the substrate and an area of the individual photosensitive areas of 0.8 to 1 mm$^2$ may be integrated into in a chip having an edge length in the range of approx. 200 µm to 300 µm, with the total chip height being approx. 400 µm to 500 µm, in an electronic component suitable for production of an optoelectronic gas sensor.

For practical use, the chip of the optoelectronic gas sensor is mounted in a casing (preferably SMD) and protected by a cover. This cover has openings over the locations coated with gas-sensitive material so that gas can penetrate.

With respect to good processability, it is possible to mount the casing cover on a circuit board before applying the gas-sensitive materials and to solder the electronic component which later forms the optoelectronic gas sensor into a corresponding electronic circuit without coating it. Therefore, the gas-sensitive materials cannot be destroyed or damaged in any way by the heat of the soldering operation. The openings in the casing cover through which the coating is subsequently applied or through which the gas enters in subsequent use can be sealed with an adhesive film, for example, in the soldering operation to prevent flux from entering.

The present invention offers at least the following advantages, in particular, in comparison with conventional optoelectronic gas sensor based on optodes:

This sensor has extremely small geometric dimensions due to the integration of all function units of the sensor (i.e., the electronic components and the optode paths on a silicon chip).

According to the first embodiment of the present invention, the optode segments, i.e., the gas-sensitive polymer and the reference segment, can assume the function of the passive optical system otherwise necessary, such as prisms or mirrors in guiding the light from the opto-transmitter to the optode and from the optode to the photodiode, because of the small distance between the opto-transmitter (LED) and the photosensitive elements (photodiodes) This guarantees that the atmosphere surrounding the gas can act on a large surface area of the optode.

The small distance between the LEDs and the photodiode causes a high efficacy in coupling light between these two components. This means a low power consumption.

The adjusted emission characteristics of the LEDs laterally, achieved by mirrorizing the top and bottom sides of them, enhances this effect.

coupling losses are extremely low, i.e., no additional passive optical system is necessary, due to direct coupling of light from the LEDs to the optode segments and the reference segment and from there to the photodiodes.

The barriers guarantee low crosstalk.

The reference and measuring branches have a high symmetry because the photodiodes are monolithically integrated.

The optoelectronic gas sensor implemented according to the second embodiment of the present invention has an advantage in comparison with that described above in that the optode layer and the layer of the reference segment can be much thinner. These layers have a thickness of approx. 5–10 µm. They do not function primarily as light guides because the light is first emitted into air by the LED and then passes through the optode layers and/or the reference layer to the photodiodes either directly or after being reflected by the surrounding casing. The barriers have only a subordinate importance here.

DETAILED DESCRIPTION

Figure 1:
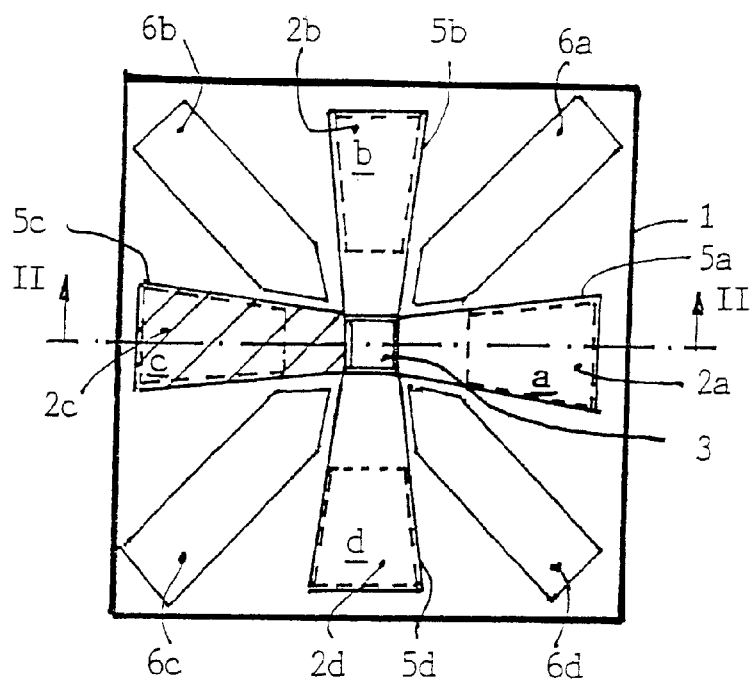
FIG. 1 shows a layout of a first embodiment of an optoelectronic gas sensor based on optodes according to the present invention.

The layout of a first embodiment of an optoelectronic gas sensor based on optodes shown schematically in FIG. 1 contains four equally large transmission branches a, b, c and d. One of the transmission branches, namely transmission branch c in this example, is designed as a reference segment, as indicated by diagonal shading. The reference segment, three optode segments, each made of optode material 5a–5d, and a photosensitive area 2a–2d of a photodiode (shown with dotted lines) below that are arranged in a star pattern around a central LED 3 on a common substrate 1. Individual transmission branches a–d are separated by barriers 6a–6d located in the interspaces between the optode segments.

Figure 2:
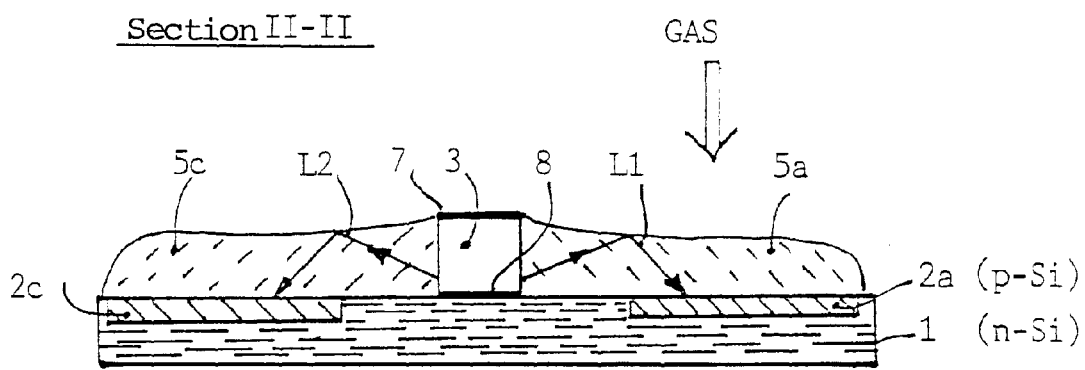
FIG. 2 shows schematically a central cross section through the gas sensor chip illustrated in FIG. 1.

The sectional view of the optoelectronic gas sensor based on optodes shown in FIG. 1, as seen along line II—II of intersection in FIG. 2, illustrates the integration of the photosensitive areas (only areas 2a and 2c are shown here) of p-type Si in substrate 1 made of n-type Si. Central LED 3 is mirrorized on its top and bottom sides with a mirror layer 7, 8 made of gold, for example, so the beams of light emitted by it are emitted mainly laterally, i.e., into the optode material of optode segments 5a and 5c, where they are totally reflected at the interface of the optode material with air, as illustrated by two beam paths L1 and L2 shown as examples, so the beams of light are thus directed at photosensitive areas 2a and 2c of the photodiodes.

As shown in FIG. 2, the optode material is applied approximately to the height of central LED 3, the areas of the optode material adjacent to both sides of the LED and/or layer 5c covering the reference segment are designed with a slight descending curve, and the outer sections of the optode segments and the reference segment are rounded to improve the total reflection of light beams L1, L2 emitted into the optode segments and the reference segment. In this way, a large portion of the light input by the LED into the optode segments and the reference segment reaches photosensitive areas 2a–2d of the photodiodes.

It should also be pointed out that barriers 6a–6d which are not shown in FIG. 2 have a height approximately up to the height of LED 3, so the individual transmission branches do not have any mutual optical influence on one another. Gas to be measured can flow over optode segments a, b, d (see arrow in FIG. 2) through windows open to the ambient atmosphere in a casing not shown in FIGS. 1 and 3.

A prototype of the optoelectronic gas sensor based on optodes according to FIGS. 1 and 2 was produced using a silicon chip with, for example, the basic structure of photodiode BPW 34 having an area of 2×2 mm$^2$ and a thickness of 250 $\mu$m as the carrier chip, but it was not designed to be photosensitive over the entire area, but instead having photosensitive areas of p-type silicon only selectively at defined locations 2a–2d (cf. FIG. 1).

An LED chip 3 as an opto-transmitter was glued to the center of the top side of the carrier chip. The LED had mirror layers 7, 8 produced by gold layers on its top and bottom sides (cf. FIG. 2). In this way, light which would otherwise be emitted by the LED with a spherical characteristic could be emitted primarily laterally. This gave a higher intensity accordingly. Optode layers 5a, 5b, 5d, designed as measuring segments, were coated with a gas-sensitive polymer, i.e., a polymer material to which an indicator substance had been added. The reference segment was preferably coated with an optode carrier material, i.e., a polymer material without any added indicator substance. The design was largely symmetrical, so that in addition to influences of the electronics, changes such as aging and soiling involving the carrier material of the optodes could also be compensated. Light (cf. L1, L2 in FIG. 2) reached the photodiode from the LED by total reflection in the optode layers and/or the reference layer. Locations of the Si chip that were coated but were not photosensitive were mirrorized by gold plating, for example, before being coated. Finally, barriers 6a–6d were preferably applied by a screen printing method which guarantees that the barrier height required for effective separation can be achieved.

The thickness of the Si chip was 250 $\mu$m, as mentioned above. The LED was 300 $\mu$m wide and 300 $\mu$m high. The barrier height was also 300 $\mu$m.

For practical use, the chip was mounted in a casing, preferably SMD, and protected by a cover having openings over the locations coated with gas-sensitive optode materials, i.e., over optode segments 5a, 5b and 5d so that gas could penetrate.

The prototype gas sensor chip had extremely small geometric dimensions due to the integration of all function units of the optoelectronic gas sensor such as the electronic components and the optodes on one silicon chip.

Because of the small distance between the LED and the optical receivers, i.e., the photosensitive areas of the photodiodes, the optode segments with the gas-sensitive polymer were able to assume the function of the passive optical system that would otherwise be necessary. This concerns the guidance of light from LED 3 functioning as the opto-transmitter to the optode and from the optode to the photodiode. This guarantees that the gas of the ambient atmosphere can act on a large surface area of the optode.

Due to the small distance between the LED and the photosensitive areas of the photodiode, a high efficacy was achieved in coupling light between these components. This resulted in a low power consumption.

The adjusted emission characteristic of the LED laterally achieved due to the mirrorized top and bottom sides of the LED enhanced this effect. Extremely low coupling losses occurred due to the direct coupling of light from the LED into the optode and from there into the photodiode. Thus, additional passive optical components could be eliminated.

The barriers created between the optode segments and the reference segment guaranteed minimal crosstalk, which would otherwise be caused by stray light that could come from the optodes and enter the adjacent optode segments. The similar and centrally symmetrical embodiment of the measuring segments and the reference segment yielded an optoelectronic gas sensor based on optodes where changes such as aging and soiling involving the carrier material of the optodes could be compensated in addition to compensating for influences of the electronics.

Of course, the square embodiment illustrated in FIGS. 1 and 2 having three optode measuring segments and one reference segment should be regarded only as an example. With similar process steps and features, it is also possible to implement chip shapes that are pentagonal, hexagonal, heptagonal, octagonal or even round, optionally having fewer than or more than three optode measuring segments.

Figure 3:
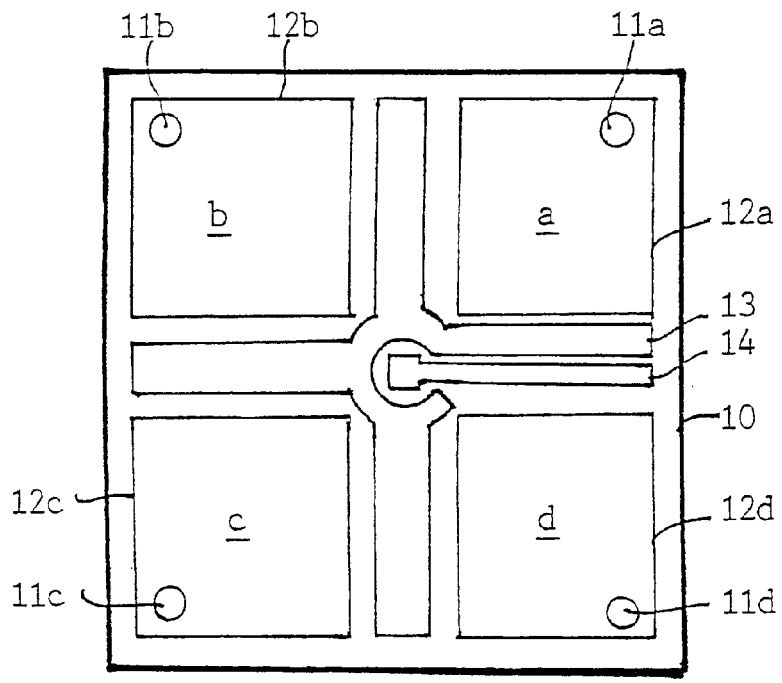
FIG. 3 shows schematically a layout of an electronic component suitable for producing an optoelectronic gas sensor based on optodes according to the present invention.
Figure 4:
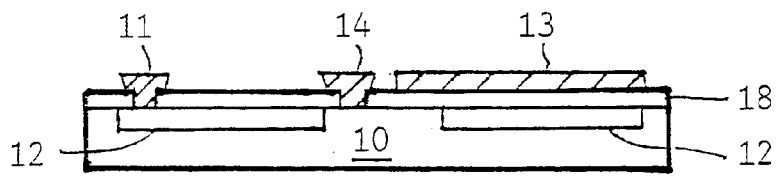
FIG. 4 shows schematically a cross section through the chip illustrated in the layout in FIG. 3.
Figure 5:
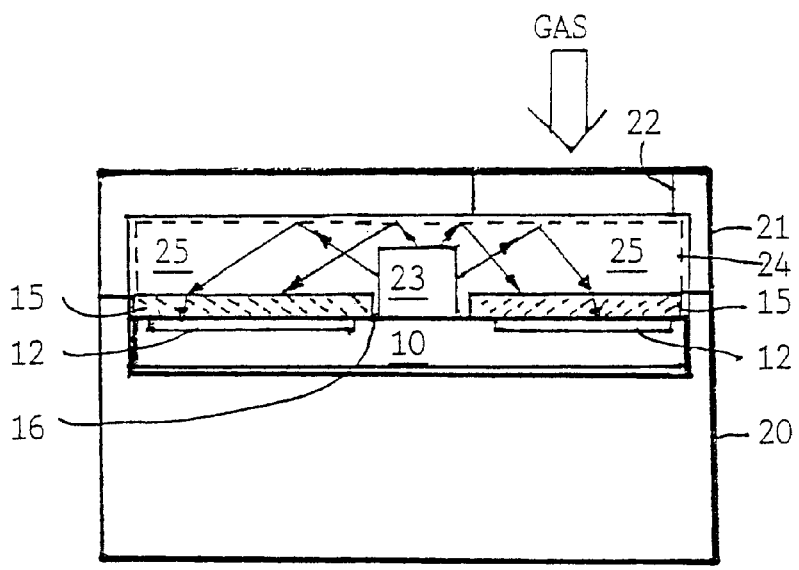
FIG. 5 shows schematically an optoelectronic gas sensor chip according to the present invention produced according to FIGS. 3 and 4 using the electronic component, having a casing surrounding it.
Figure 6:
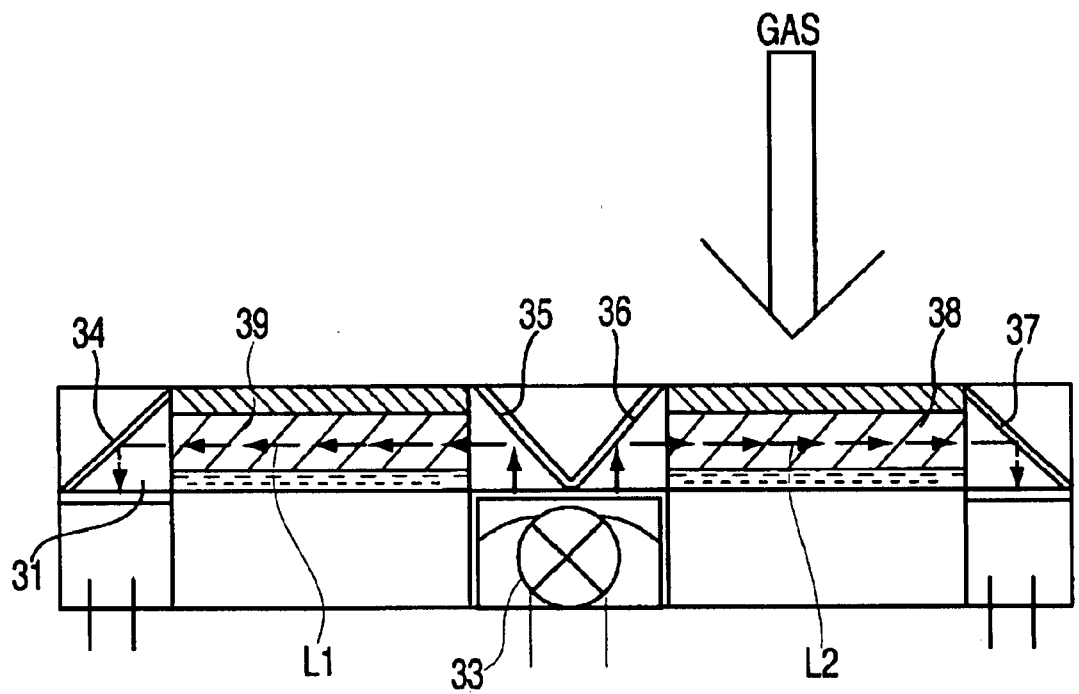
FIG. 6 shows an optoelectronic gas sensor chip.
Figure 7:
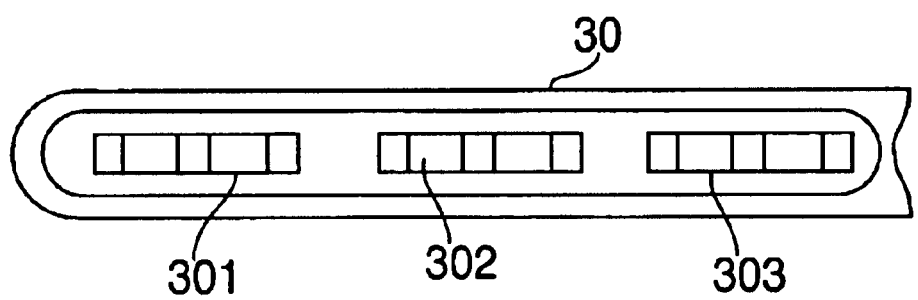
FIG. 7 shows a gas measuring sensor produced with the optoelectronic gas sensor chip of FIG. 6.

FIGS. 3 through 5 show one embodiment of an electronic component which is also suitable for a customer-specific design of an optoelectronic gas sensor based on optodes according to the present invention.

The layout illustrated in FIG. 3 shows that, as in the first embodiment described above and illustrated in FIGS. 1 and 2, four photosensitive areas 12a–12d are integrated on a substrate 10, e.g., made of n-type silicon, and together with an optode material not shown in FIGS. 3 and 4 and/or a reference layer to be applied later by the customer, they form four transmission branches a, b, c and d.

Photosensitive areas 12a–12d are integrated on square silicon substrate 10 in the form of square photosensitive elements made of p-type Si so that they maintain a certain spacing.

Metallizing strips 13 and 14 are arranged in the interspaces between photosensitive elements 12a–12d, providing the electric connection to an LED to be glued in place later and functioning as the opto-transmitter, Contact pads 11a–11d are provided for contacting photosensitive elements 12a–12d.

As shown by the sectional view in FIG. 4, contact pads 11 and the central end of metallizing strip 14 are contacted through contact openings through an insulation layer 18 made of SiO$_2$, for example, covering substrate 10 and photosensitive elements 12, in each case to photosensitive elements 12 of p-type Si or to substrate 10 of n-type Si.

The electronic component illustrated in FIGS. 3 and 4 has a chip edge length of approx. 250 $\mu$m, and the area of the individual photosensitive areas amounted to approx. 0.8–1 mm$^2$. The metallization was gold or aluminum.

Use of the electronic component illustrated in FIGS. 3 and 4 is especially suitable for producing an optoelectronic gas sensor based on optodes.

This will now be explained on the basis of FIG. 5.

The chip is mounted in a casing 20 (preferably SMD) and protected by a cover 21. Cover 21 has openings 22 over the locations to be coated with gas-sensitive materials, so that gas can penetrate (see arrow). For good processability, casing cover 21 can be soldered into a suitable electronic circuit on a circuit board before applying the gas-sensitive materials, and the component shown in FIGS. 3 and 4 can be soldered there without being coated. Since the chip had not yet been coated with the gas-sensitive materials, they are protected from the soldering operation. In the case of a customer-specific implementation, the coating is applied by the customer on site through openings 22 in casing cover 21 through which the gas enters in later use. These can be sealed with an adhesive film during the soldering operation, for example, to prevent the penetration of flux.

FIG. 5 shows the finished optoelectronic gas sensor chip based on optodes. To simplify the drawing, all the metallized segments have been omitted.

Photosensitive elements 12 arranged in one plane are covered with a much thinner layer 15 of the optode material or reference segment material than was the case in the embodiment illustrated in FIGS. 1 and 2. Due to an annular gap 16, a central opto-transmitter 23 is arranged a distance away from the sections of the optode material and projects far above the top surface of optode material 15. The inside wall of casing cover 21 has a mirrorized surface 24. In this way, light emitted by LED 23 is first emitted into air, i.e., to the gas atmosphere in chamber 25 above optode layers 15, and then reaches photosensitive elements 12 through optode material 15 either directly or after being reflected on the inside wall or on mirrorized inside wall 24 of casing cover 21.

To illustrate this, FIG. 5 shows a few light beams reflected on mirror layer 24. It is noticeable here that the top side of LED 23 is not mirrorized in the embodiment according to FIG. 5. The height of central LED 23 shown in FIG. 5 is about 300 $\mu$m, as in the embodiment illustrated in FIGS. 1 and 2, while the layer thickness of optode layers 15 and the reference layer in FIG. 5 is 5–10 $\mu$m, i.e., is much thinner than the optode layer of the embodiment shown in FIGS. 1 and 2, because the optodes and the reference layer do not function primarily as light guides.

The barriers are not shown in FIG. 5 for clarity.

The photodiode array shown in FIGS. 3 and 4 and used in FIG. 5 can be produced in a size of 2×2 mm$^2$ smaller with traditional thin-film processes with standard process dimensions. Additional designs such as a pentagon, a hexagon, a heptagon, an octagon or even a circular shape can also be implemented with the embodiment illustrated in FIGS. 1 and 2.

LED 23 can be glued in place with a conductive silver adhesive applied by screen printing. The barriers not shown in FIG. 5 can also be applied by a similar screen printing operation using a conductive silver adhesive at a height of approx. 50 $\mu$m.

At least the following advantageous properties may apply to the embodiment of an optoelectronic gas sensor based on optodes illustrated in FIG. 5: the sensor has extremely small geometric dimensions due to the integration of all of its function units on one Si chip; due to the small distance between LED 23 and photodiodes 12, the optode made of the gas-sensitive polymer makes a passive optical system unnecessary (apart from possible mirrorizing of the inside wall of casing cover 21).

This guarantees that the gas flowing through windows 22 into interior space 25 can act on a large optode surface. Here again, a high efficacy in coupling light between the components is achieved due to the small distance between LED 23 and photodiodes 12, which causes a low power consumption.

What is claimed is:

1. An optoelectronic gas sensor, comprising:
   separate photosensitive elements disposed in a single plane in a semiconductor substrate;
   an opto-transmitter disposed centrally between the photosensitive elements, the opto-transmitter and the photosensitive elements being integrated at least one of into and onto the semiconductor substrate, the opto-transmitter having a lateral emission area, the lateral emission area emitting light laterally from the opto-transmitter
   sections of an optode material covering the lateral emission area and the photosensitive elements, the optode material forming transmission branches, the optode material having a thickness and a refractive index such that light emitted laterally from the lateral emission area is guided to the photosensitive elements by total reflection in the optode material via the transmission branches; and
   barriers separating the individual transmission branches and disposed between the photosensitive elements.

2. An optoelectronic gas sensor, comprising:
   separate photosensitive elements disposed in a single plane in a semiconductor substrate;
   sections of an optode material covering the photosensitive elements; and
   an opto-transmitter disposed centrally between the photosensitive elements, the opto-transmitter and the photosensitive elements integrated at least one of into and onto the semiconductor substrate, the opto-transmitter being spaced a distance away from the sections of the optode material via an annular gap, the opto-transmitter having a height that is much larger than a thickness of the optode material, the opto-transmitter emitting light into air before reaching the photosensitive elements through the optode material at least one of directly and after being reflected on inside walls of a casing surrounding a gas sensor chip.

3. The optoelectronic gas sensor according to claim 1, wherein one of the photosensitive elements and the optode material covering the one of the photosensitive elements form a reference segment.

4. The optoelectronic gas sensor according to claim 1, wherein the optode material includes a gas-sensitive polymer carrier material to which an indicator substance is added.

5. The optoelectronic gas sensor according to claim 3, wherein the reference segment is covered by a layer including a polymer carrier material without an added indicator substance.

6. The optoelectronic gas sensor according to claim 1, wherein the photosensitive elements and the sections of optode material covering the photosensitive elements are arranged in sectors having central symmetry around the opto-transmitter.

7. The optoelectronic gas sensor according to claim 1, wherein the photosensitive elements and the sections of optode material covering the photosensitive elements form four transmission branches, the four transmission branches including three sensor segments and one reference segment.

8. The optoelectronic gas sensor according to claim 1, wherein the barriers have a height such that the barriers shield stray light coming from the optode material covering one photosensitive element with respect to adjacent optode material covering another photosensitive element.

9. The optoelectronic gas sensor according to claim 8, further comprising:
   a mirror layer covering side faces of the barriers and areas on the semiconductor substrate which are not photosensitive.

10. The optoelectronic gas sensor according to claim 1, wherein the semiconductor substrate includes an n-type silicon substrate, and
   wherein the photosensitive elements include a p-type silicon material.

11. The optoelectronic gas sensor according to claim 1, wherein the photosensitive elements form photodiodes, and
   wherein the opto-transmitter is a light emitting diode (LED).

12. The optoelectronic gas sensor according to claim 1, further comprising:
   a cover protecting a chip of the optoelectronic gas sensor, the cover including openings over gas-sensitive transmission branches so that the optode material of the gas-sensitive transmission branches are exposed to the gas that is being measured.

13. The optoelectronic gas sensor according to claim 1, wherein the thickness of the optode material is between approximately 200 microns and approximately 300 microns.

14. The optoelectronic gas sensor according to claim 1, wherein the thickness of the optode material is between approximately 220 microns and approximately 260 microns.

15. The optoelectronic gas sensor according to claim 2, wherein the thickness of the optode material is between approximately 5 microns to approximately 20 microns, and
   wherein the height of the opto-transmitter is approximately 300 microns.

16. The optoelectronic gas sensor according to claim 2, wherein the thickness of the optode material is between approximately 5 microns to approximately 10 microns, and
   wherein the height of the opto-transmitter is approximately 300 microns.

17. An electronic component for use in producing an optoelectronic gas sensor, comprising:
   separate photosensitive elements integrated at least one of into and onto a semiconductor substrate in sectors with central symmetry while maintaining a spacing;
   a thin dielectric insulation layer covering photosensitive semiconductor areas;
   contact openings being provided with contacts to the photosensitive semiconductor elements at defined peripheral locations on the photosensitive semiconductor elements; and
   metallized strips being provided in spaces between the photosensitive elements and leading to a central contact pad for connecting an opto-transmitter.

18. The electronic component according to claim 17, wherein the opto-transmitter is an LED.

19. The electronic component according to claim 17, wherein the photosensitive elements include four photodiodes, the four photodiodes including a common cathode and individual photosensitive areas, the common cathode being formed by the semiconductor substrate, the individual photosensitive areas each being between approximately 0.3 $mm^2$ and approximately 0.8 $mm^2$, the four photodiodes being in a chip, the chip having an edge length that is between approximately 200 microns and approximately 300 microns and a height that is between approximately 200 microns and approximately 300 microns, the chip being metallized with at least one of gold and aluminum.

20. The electronic component according to claim 19, wherein each of the four photodiodes is the same size.

* * * * *